United States Patent [19]
Waxman et al.

[11] Patent Number: 5,429,598
[45] Date of Patent: Jul. 4, 1995

[54] SURGICAL ACCESS DEVICE AND PROCEDURE

[75] Inventors: Kenneth Waxman, Laguna Hills; Charles C. Hart, Huntington Beach, both of Calif.

[73] Assignee: Applied Medical Resources Corporation, Laguna Hills, Calif.

[21] Appl. No.: 230,165

[22] Filed: Apr. 19, 1994

[51] Int. Cl.[6] ............................................. A61M 31/00
[52] U.S. Cl. ..................................... 604/51; 604/164; 604/174
[58] Field of Search ................. 604/104, 96, 164, 165, 604/167, 169, 170, 51, 53, 158; 606/220, 108

[56] References Cited

U.S. PATENT DOCUMENTS

| | | |
|---|---|---|
| Re. 34,021 | 8/1992 | Mueller et al. |
| 5,071,405 | 12/1991 | Piontek et al. |
| 5,151,086 | 9/1992 | Duh et al. ............................ 604/51 |
| 5,167,627 | 12/1992 | Clegg et al. ..................... 604/164 X |
| 5,250,025 | 10/1993 | Sosnowski et al. ................... 604/51 |
| 5,279,553 | 1/1994 | Winkler et al. .................. 604/164 X |
| 5,281,204 | 1/1994 | Horie et al. ..................... 604/174 X |

OTHER PUBLICATIONS

"Laparoscopic Placement of Gastrostomy Feeding Tube", Ross Product Division, Abbott Laboratories, Mar. 1993. (product brochure).

"18 French Flexiflo Lap G", Ross Product Division, Abbott Laboratories, 1993, (product brochure).

*Primary Examiner*—John D. Yasko
*Attorney, Agent, or Firm*—Richard L. Myers

[57] ABSTRACT

A combination for accessing a body conduit includes a trocar for creating a hole into the body conduit. A cannula included in the trocar has a cylindrical wall with an outside diameter and an inside diameter. An elastomeric tube having a channel extending between a proximal end and a distal end is movable between a normal state wherein the tube has a first outside diameter greater than the outside diameter of the cannula and a stretched state wherein the tube has a second outside diameter less than the inside diameter of the cannula. A stylet having a length longer than the length of the tube in the normal state engages the tube at its distal end and is operable to move the tube from the normal state to the stretched state permitting the tube to be inserted into the cannula and through the cannula into the body conduit. The stylet and cannula can then be removed from the tube leaving the tube extending through the hole into the body conduit with the tube in the normal state and its first outside diameter filling the hole left by the smaller outside diameter of the cannula. An associated method includes the steps of stretching the tube along the stylet from the normal state to the stretched state and inserting the stretched tube through the cannula into the body conduit. The stylet is then removed from the tube leaving the tube in the cannula. Finally, the cannula is removed from the tube leaving the tube extending percutaneously through the abdominal wall and into the body conduit of the patient.

20 Claims, 4 Drawing Sheets

SURGICAL ACCESS DEVICE AND PROCEDURE

BACKGROUND OF THE INVENTION

1. Field of the Invention

This invention relates generally to apparatus and methods for providing percutaneous access to an internal body conduit and relates more specifically in one aspect of the invention to apparatus and methods for providing percutaneous access through a gastrostomy tube directly into the stomach of a patient.

2. Discussion of the Prior Art

Tubes are used to provide direct access into internal organs, cavities and other conduits of patients, for a variety of reasons. In one application, a feeding tube is placed in the stomach, duodenum, intestine or colon of a patient in order to provide access for the direct administration of liquid diet or medication. This may be required due to some problem of the patient associated with his ability to chew, swallow, or otherwise ingest nutrients into the stomach through the normal channel including the mouth, throat, esophagus and hiatal valve.

There are four standard methods for placement of a feeding tube. In perhaps the most certain method of placement, an open surgical technique is used. In this method, the feeding tube is placed, under direct visualization, through a surgical incision in the abdominal wall, and into the organ. The organ is then pulled into proximity with the abdominal wall and anchored in a process commonly referred to as approximation. This step of approximation is also performed under direct visualization which allows the surgeon to adjust the anchoring tension in order to achieve the best contact and pressure between the organ and the abdominal wall. While this open procedure best facilitates approximation, it nevertheless leaves the patient with a sizable incision and a long recovery period. This is also a time consuming procedure which must be performed in the operating room. These two factors elevate the cost of the procedure significantly.

In a much less expensive procedure, nasal gastric tubes have been used to provide access to the stomach. In this case a tube is introduced into the nasal cavity of the patient, past the throat and into the stomach. This procedure need not be accomplished in the operating room, so it is much less expensive. Nevertheless, the patient is required to swallow at an appropriate time in order to pass the tube through the throat. If this passage is not accurately accomplished the tube can lodge in the lungs causing the patient to undergo considerable trauma and even producing pneumonia. Some practitioners are more skilled at this process of tube passage than others, but even these practitioners have a success rate of only about 50%. A nasal gastric tube must be taped to the side of the patient's face, often leading to sever adhesive burns. Also, in some cases the patient must be restrained in order to prevent the self-removal of this tube. Nasal gastric tubes are generally for short term use. They are usually converted to gastrostomy feeding tubes if the period needs to be extended.

In a procedure commonly referred to as percutaneous endoscopic gastrostomy (PEG) a gastroscope is placed through the mouth of the patient and into the stomach. The scope is then deflected toward the abdominal wall where the light from the scope helps identify the ideal location to access the stomach. Using a percutaneous introducer, a guidewire is inserted into the stomach through the abdominal wall; anchors are then placed across the abdominal wall and into the stomach. The tip of the guidewire is grasped through the working channel of the scope and pulled with the scope through the patient's mouth. A feeding tube is then attached to the guidewire using sutures and is pulled into place as the guidewire is withdrawn from the abdomen.

The disadvantage of this percutaneous endoscopic procedure is that the approximation of the abdominal wall with the stomach is performed without visualization. If too much tension is applied to the anchors, circulation is impaired leading to tissue necrosis. If too little tension is applied to the anchors, poor sealing contact results. In either case leakage of gastric juices around the tube can lead to inflammation and infection.

Radiologic placement has also been attempted under fluoroscopic vision. A percutaneous introducer is placed in the stomach through the abdominal wall and anchors are suitably applied. The guidewire is introduced into the stomach through an introducer which is then removed. Successive dilators can then be introduced over the guidewire until a suitably sized split-sheath can be placed. The feeding tube is then introduced through the sheath and into the stomach. Ultimately the sheath is retracted and split apart around the feeding tube. This procedure also suffers from the lack of visualization during the approximation step.

SUMMARY OF THE INVENTION

In accordance with the present invention, these deficiencies of the prior art apparatus and methods are overcome in a laparoscopic technique. Under laparoscopic visualization, a trocar is placed through the abdominal wall at a desired location for the feeding tube. The stomach, or other body conduit of interest, is pulled toward the abdominal wall by operation of a laparoscopic grasper through the trocar. The stomach is inflated through a esophageal tube and anchors are placed percutaneously into the Stomach. After the stomach is pulled toward the abdominal wall, the grasper is removed from the trocar cannula and replaced with an electrosurgical obturator.

The trocar obturator assembly is then advanced to contact the stomach wall at the desired location of the feeding tube. The assembly is advanced through the stomach wall by activating the trocar with electrosurgical power. This enables the trocar to penetrate the fibrous but supple stomach wall with a low force of entry.

The obturator is then removed from the cannula and a feeding tube is prepared for insertion. This feeding tube will commonly have a central channel extending between a proximal end and a distal end. The channel is plugged or otherwise blocked at the distal end of the tube in proximity to an anchoring tip which normally is disposed in a high profile state. A stylet inserted into the central channel engages the plug or block at the distal end of the tube. Stretching the tube along the stylet moves the tube and particularly the anchoring tip into a stretched low profile state.

A locking mechanism disposed between the tube and the stylet maintains this stretched low profile state during insertion of the feeding tube through the cannula and into the stomach. Once the feeding tube is in place, the stylet can be unlocked and removed from the feeding tube thereby permitting the anchoring tip of the tube to deploy to a normal high profile state within the stomach. The cannula of the trocar can then be removed over the proximal end of the feeding tube leaving the feeding tube extending through the abdominal wall into the stomach. Alternatively the cannula can be removed first followed by removal of the stylet.

Several advantages result from this procedure. Importantly, the tube in its natural state can have an outside diameter which is larger than that of the trocar. Even though the tube in its stretched state will have a reduced diameter permitting the tube to be inserted through the trocar cannula, once the cannula is removed the tube is free to expand to its natural diameter which will typically be larger than the diameter of the hole left by the trocar. This size differential tends to form strong seals between the feeding tube and the walls of the stomach and abdomen.

It is also of considerable advantage that this procedure can be accomplished under endoscopic vision. This enables the stomach to be carefully positioned in the critical approximation step next to the abdominal wall. Under visualization, this approximation can be achieved with a sufficiently tight relationship to accomplish the necessary sealing, but with a sufficiently loose relationship to facilitate blood circulation.

This highly effective procedure which develops synergies with the novel tube/stylet combination and the electrosurgical trocar, is equally advantageous for providing percutaneous access into any organ, cavity, or other body conduit. In one aspect, the invention includes a combination comprising a trocar for creating a hole into a body conduit. A cannula included in the trocar has a cylindrical wall with an outside diameter and an inside diameter. The combination also includes an elastomeric tube having a channel extending between a proximal end and a distal end, the tube having in a normal state a first outside diameter greater than the outside diameter of the cannula and having in a stretched state a second outside diameter less than the inside diameter of the cannula. A stylet is sized and configured to engage the tube at the distal end of the tube. The stylet is operable to move the tube from the normal state to the stretched state so the tube can be inserted into the cannula and through the cannula into the body conduit. This combination enables the stylet and cannula to be removed from the tube leaving the tube in the normal state with its larger first outside diameter filling the hole left by the smaller outside diameter of the cannula.

In another aspect of the invention the combination includes a tube having an elongate configuration and an axis extending between a proximal end and a distal end. The tube has walls defining a lumen along the axis and elastomeric characteristics permitting the tube to be stretched axially between a normal state and a stretched state. In the normal state the tube has a high profile wherein the walls of the tube have a first length and a first outside diameter. In the stretched state, the tube has a low profile and the walls of the tube have a second length greater than the first length and a second outside diameter less than the first outside diameter. A plug disposed along the axis of the tube at the distal end of the tube has a generally fixed relationship with the walls of the tube. An elongate stylet has a proximal end and a distal end separated by a length greater than the first length of the tube in the normal state. This stylet is sized and configured to be inserted into the proximal end of the tube along the lumen of the tube to bring the distal end of the stylet into engaging relationship with the plug at the distal end of the tube. A connector includes a first connector portion and a second connector portion which is adapted to be releasibly locked to the first connector portion. The first connector portion is attached to the proximal end of the tube while the second connector portion is attached to the proximal end of the stylet. The tube has properties for being stretched along the stylet from its normal high profile state to its stretched low profile state. Means is included in the connector for releasibly locking the first portion of the connector to the second portion of the connector to maintain the tube in its stretched, low profile state.

In a further aspect of the invention, a method is disclosed for inserting a medical device through a hole and having a particular diameter, and into a body conduit. The method includes the steps of providing the medical device in the form of an elongate tube with an axis extending between a proximal end and a distal end. The tube has walls defining a lumen along the axis and elastomeric characteristics permitting the tube to be stretched axially between a natural state and a stretched state. In the natural state the walls of the tube have a high profile, a first length and a first outside diameter. In the stretched state, the walls have a low profile with the second length greater than the first length and a second outside diameter less than the first outside diameter. The method also includes the steps of providing a stylet having a proximal end and a distal end separated by a length greater than the first length of the tube in the natural state. Engaging the distal end of the tube with the distal end of the stylet and stretching the tube by moving the proximal end of the tube along the stylet moves the tube to the stretched low profile state. The proximal end of the tube can then be locked to the stylet with the tube in the stretched low profile state. The method includes the step of inserting the stylet and the tube in the stretched state to the whole in the body conduit. The proximal end of the tube unlocked from the stylet to permit the tube to return to the natural high profile state. The distal end of the stylet is then disengaged from the distal end of the tube and the stylet removed from the hole leaving the tube extending through the hole into the body conduit with the tube in the natural high profile state.

In a further aspect of the invention, a method is disclosed for placing a catheter percutaneously into a body conduit disposed Within the abdominal wall of a patient. The method includes the step of providing the trocar including a cannula and an obturator, the cannula having a proximal wall with an outside diameter and an inside diameter. The trocar is inserted through the abdominal wall and into the body conduit of the patient. Removing the obturator from the cannula opens the working channel of the trocar. A catheter is provided in the form of an elastomeric tube having a channel extending along the length of the tube between a proximal end and a distal end. The tube has in a normal state a first outside diameter greater than the outside diameter of the cannula and in a stretched state a second outside diameter less than the inside diameter of the cannula. A stylet is provided having a length extending between a proximal end and a distal end. The length of the stylet is greater than the first length of the tube in the normal state. The tube is stretched along the stylet from the normal state to the stretched state and inserted through the cannula of the trocar into the body conduit. The stylet can then be removed from within the tube. This step can be preceded or followed by removal of the cannula over the tube. In either case the tube is left to extend percutaneously through the abdominal wall and into the body conduit of the patient.

These and other features and advantages of the invention will be more apparent with a description of preferred embodiments and reference to the associated drawings.

DESCRIPTION OF PREFERRED EMBODIMENTS AND BEST MODE OF THE INVENTION

Figure 1:
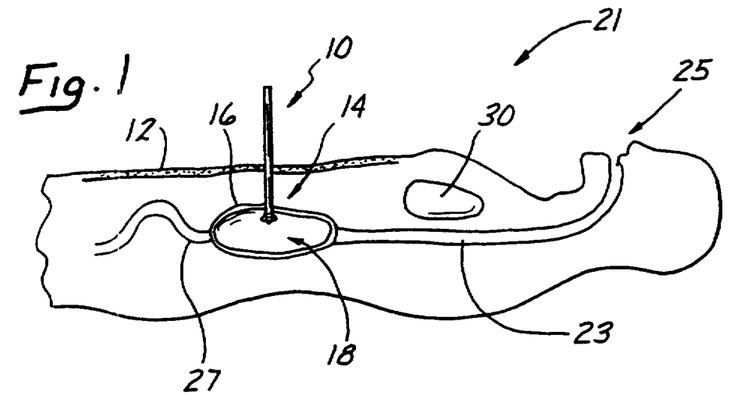
FIG. 1 is a side view of a patient illustrating a feeding tube of the present invention percutaneously accessing the stomach cavity of the patient.

A gastrostomy feeding tube is illustrated in FIG. 1 and designated generally by the reference numeral 10. The tube 10 is positioned to extend through an abdominal wall 12 into an abdominal cavity 13 of a patient 14. Within the cavity 13 the tube 10 extends toward a stomach 15, through a stomach wall 16, and into a stomach cavity 18. In a normal manner, the patient 14 includes an esophagus 23 which extends from a mouth 25 into fluid communication with the stomach cavity 18.

The gastrostomy tube 10 is representative of any device which provides percutaneous access to the interior regions of the patient 14. It may comprise a tube providing access with the interior regions for fluids, or it may provide access for other apparatus such as an electrical conductor or other surgical instruments. The stomach 15 is representative of any body conduit in the digestive tract, such as the esophagus 23 or intestine 27, and or any other body conduit, cavity or organ of the patient 14, such as a bladder 30. In FIG. 1, the gastrostomy tube 10 provides direct percutaneous access into the stomach cavity 18 thereby permitting the introduction of dietary nutrients and medication directly into the digestive tract.

Figure 2:
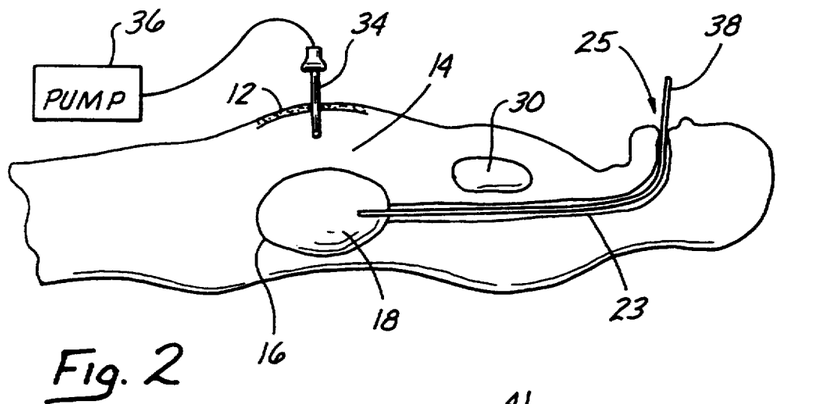
FIG. 2 is a side view of the patient illustrating the insufflation of the body cavity and the inflation of the stomach cavity.

Placement of the gastrostomy tube 10 or other access device into the stomach 15 or other body conduit, can be accomplished in accordance with the method and apparatus illustrated in the remaining drawings. In FIG. 2, an insufflation or Veress needle 34 can be inserted through the abdominal wall 12 into the abdominal cavity 13. This needle 34 provides access into the abdominal cavity 13 permitting a pump 36 to introduce a pressurized gas, such as carbon dioxide directly into the cavity 13. This process, commonly referred to as insufflation, increases the volume of the cavity 13 providing an enlarged working area for laparoscopic surgery.

The wall 16 of the stomach 15 is approximately ⅛ to ¼ inch in thickness and is highly fibrous making it relatively tough. At the same time, the stomach wall 18 is very supple. These characteristics combine to make the stomach wall 16 relatively difficult to penetrate particularly by way of a puncture. For these reasons, it may be desirable in a particular procedure to inflate the stomach cavity 18, for example by way of an esophageal tube 38 extending through the mouth 25 and the esophagus 23.

Figure 3:
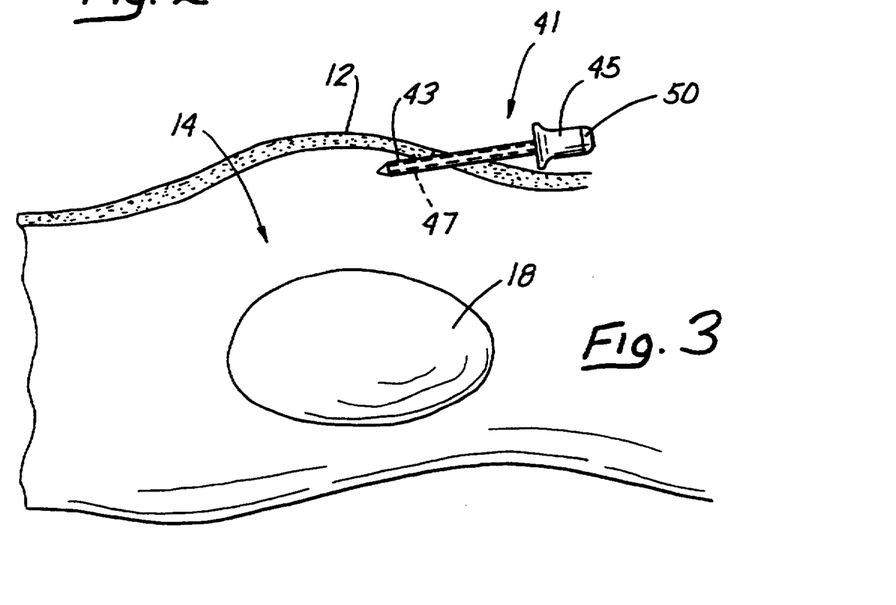
FIG. 3 is a side view of the abdominal cavity illustrating a step whereby a trocar is inserted through the abdominal wall to facilitate endoscopic visualization.

As in many laparoscopic procedures, visualization is provided by means of a scope placed through a trocar 41 which can be inserted through the abdominal wall 12 into the cavity 13. This trocar 41 will typically include a cannula 43 having a seal housing 45 and an obturator 47 having a handle 50. The obturator 47 can generally be of any type, such as the mechanical or electrosurgical varieties.

Once the trocar 41 is in place across the abdominal wall 12, the obturator 47 can be removed leaving the cannula 43 with the associated working channel 53 providing percutaneous access into the abdominal cavity 13. The initial placement of this trocar 41 facilitates the important visualization of all future steps in the process. To provide this visualization, an endoscope 61 can be inserted into the working channel 53 of the cannula 43. Images present at the distal end of the endoscope 61 are transmitted by way of a cable 63 for display on a monitor 65.

Figure 4:
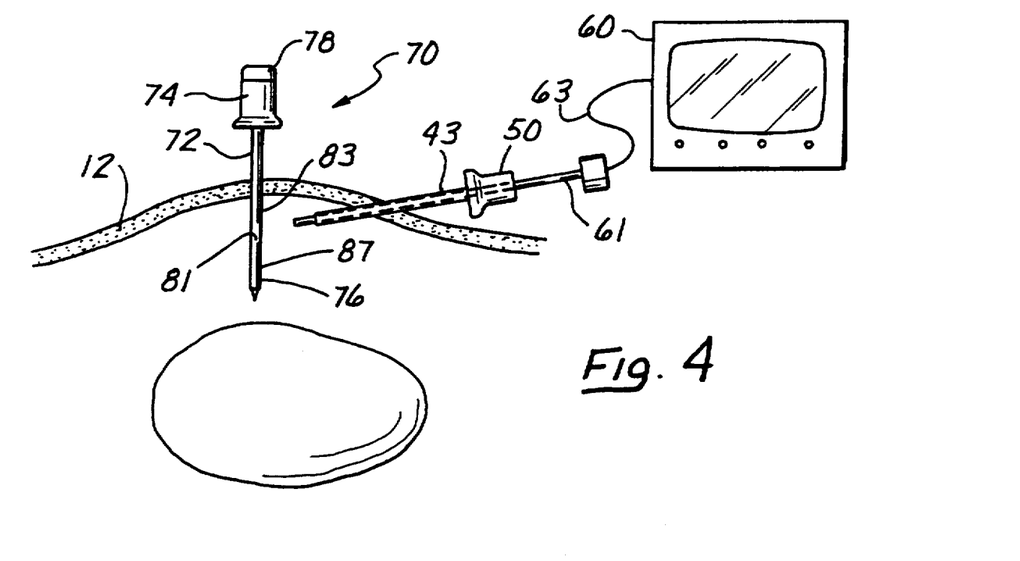
FIG. 4 is a side view similar to FIG. 3 and illustrating a step for placement of a second trocar through the abdominal wall.

Also illustrated in FIG. 4 is a second trocar 70 including a cannula 72 having a seal housing 74 and an obturator 76 having a handle 78. The cannula 72 of the second trocar 70 has a cylindrical configuration with an inner surface 81 defining a working channel 83 with an inside diameter, and an outer surface 87 defining an outside diameter of the cannula 72. Although the obturator 76 can be of the mechanical variety, an electrosurgical obturator is of particular advantage for the reasons discussed in greater detail below. Such an electrosurgical obturator is disclosed and claimed in applicant's copending application Ser. No. 08/156,958 filed on Nov. 22, 1993 and entitled Electrosurgical Trocar. The electrosurgical obturator 76 enables the trocar 70 to be inserted with a relatively small axial force thereby facilitating placement of the cannula 72 across the abdominal wall 12.

Figure 5:
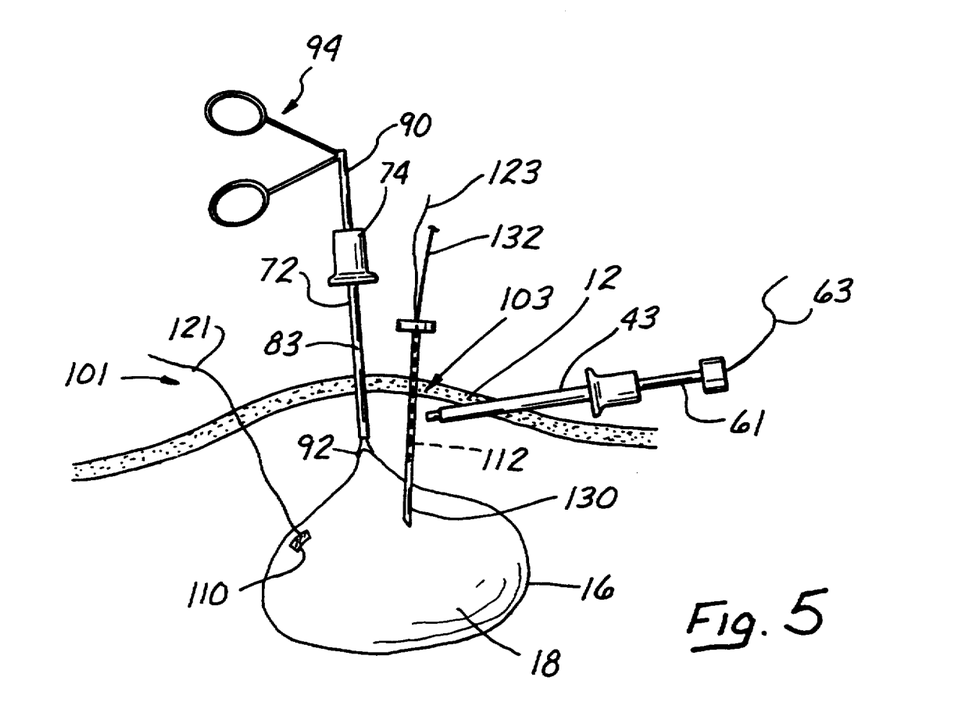
FIG. 5 is a side view similar to FIG. 3 illustrating the steps of grasping, drawing and anchoring the stomach in proximity to the abdominal wall.

At this point, the obturator 76 can be removed from the cannula 72, and pair of laparoscopic graspers 90 can be inserted through the working channel 83 as illustrated in FIG. 5. The graspers 90 have a pair of serrated jaws 92 which can be opened and closed by operation of scissor handles 94. Moving the graspers 90 axially through the working channel 83 brings the jaws 92 into proximity with the stomach wall 16. Then, by operation of the handles 94, the jaws can be opened and closed to grasp the stomach wall 16. Axial retraction of the graspers 90 through the cannula 72 moves the stomach 15 into proximity with the abdominal wall 12.

Figure 6:
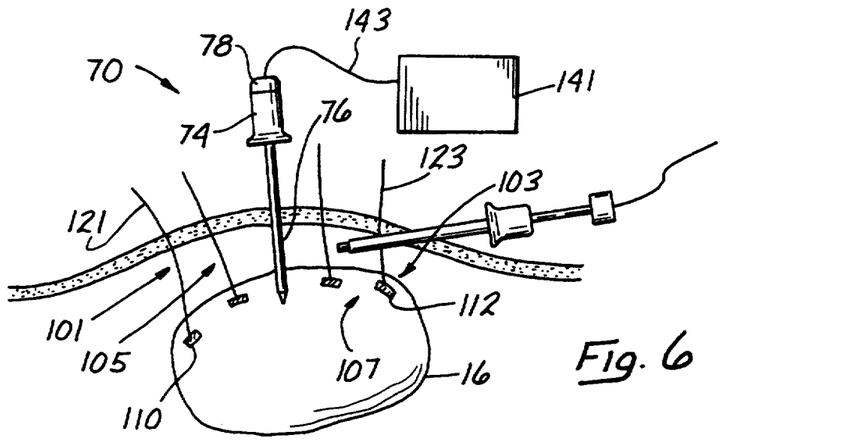
FIG. 6 is a side view similar to FIG. 3 illustrating further operation of the second trocar to penetrate the stomach wall.

A plurality of anchors, such as the four anchors illustrated in FIG. 6 and designated by the odd reference numbers 103-107, can be used to maintain the stomach wall 18 in this proximal location. Two of the anchors 101 and 103 are illustrated in FIG. 5 each including a T-bar 110 and 112, respectively, and an associated suture 121 and 123, respectively.

The anchors 101-107 can be placed using an access needle 130 which is inserted percutaneously through the abdominal wall 12 and the stomach wall 16. As illustrated with reference to the anchor 103, the T-bar 112 with its associated suture 123 can be inserted into the needle 130 and forced through the needle with a wire 132. Once the T-bar 112 clears the distal end of the needle 130 it will deploy in a generally parallel relationship to the wall 16, and the needle 130 can be removed over the suture 123.

With the anchors 101-107 suitably positioned as illustrated in FIG. 6, the graspers 90 can be removed and the obturator 76 reinserted into the cannula 72 as illustrated in FIG. 6.

At this point in the process, it is desirable to puncture the stomach wall 16. This wall 16 is relatively tough since it has a substantial thickness of ⅛ to ¼ inch and a general fibrous consistency. The stomach wall 16 also is very supple. These two characteristics of the stomach make it most difficult to puncture the stomach using an ordinary mechanical trocar.

It has been found that an electrosurgical trocar of the type previously discussed offers exceptional advantages to this step of the process. In this case, the obturator 76 is energized by high frequency current from a generator 141 which is introduced to the obturator 76 through a cable 143. Energizing the electrosurgical obturator with this high frequency current tends to vaporize the cells of the stomach wall 16 effectively cutting the wall prior to its penetration by the trocar 70.

Figure 7A:
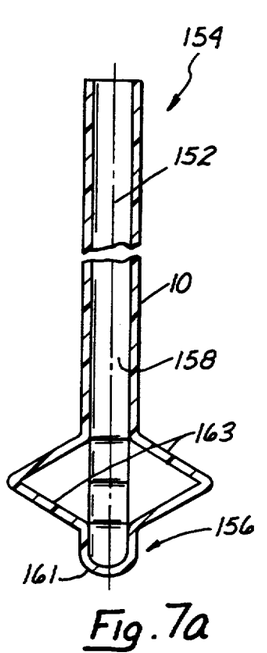
FIG. 7a is a side elevation view of a gastrostomy tube shown in its normal high profile state and including anchor means in the form of a plurality of fingers.

A preferred embodiment of the feeding tube 10 is illustrated in FIG. 7a. This tube 10 has an elongate configuration which is defined by an axis 152 extending between a proximal end 154 and a distal end 156. The tube 10 is preferably molded from latex, natural rubber, or any other material having generally elastomeric characteristics. The tube 10 is provided with a central lumen 158 along the axis 152 which is open at the proximal end 154 but at least partially closed at the distal end 156. The closure at the distal end can be implemented for example by a plug or wall 161 which at least partially blocks the lumen 158. This wall 161 extends generally transverse, such as perpendicular, to the axis 152 and effectively closes the lumen 158.

Supporting the wall 161 at the distal end 156 of the tube 10 are a plurality of fingers 163, perhaps four in number, which are equally spaced around the circumference of the tube 10 and extend generally radially outwardly in the normal high profile state illustrated in FIG. 7a. These fingers 163 define intervening slots 165 which are in fluid communication with the lumen 158. Accordingly, the lumen 158 and slots 165 provide a channel through which the patient 14 can be fed liquid nutrients and medications.

Figure 7B:
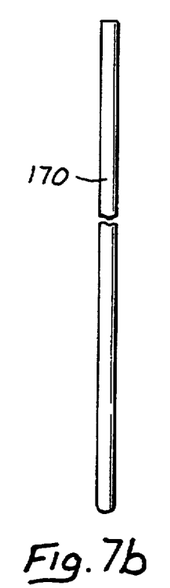
FIG. 7b is a side elevation view of a gastrostomy tube shown in its normal high profile state and including anchor means in the form of a balloon.

Equally applicable to the present invention is a feeding tube such as that illustrated in FIG. 7b. In this case, the feeding tube 10 includes anchor means in the form of a balloon 165. This balloon is inflatable through an inflation channel 166 and an inflation hole 167 beneath the balloon 165. In this case, the feeding tube 10 in its normal state has a high profile along the length of the tube 10 but the balloon 165 is in a deflated state. Expansion of the balloon 165 is achieved when the balloon is inflated in order to anchor the feeding tube 10 in the stomach 15. The feeding tube 10 of FIG. 7b also includes the central channel 158 and a plurality of holes 168 through which the nutritive fluids can be administered.

A stylet 170 is illustrated in FIG. 7c to have a generally elongate configuration. The stylet 170 preferably has a length greater than that of the feeding tube 10 in the normal high profile state illustrated in FIG. 7a. In a preferred embodiment wherein the tube 10 in the normal state has the length of about 9.5 inches, the stylet has a length of about 15 inches. Where the diameter of the lumen 158 is about 0.2 inches, the diameter of the stylet is preferably 0.125 inches.

Figure 8:
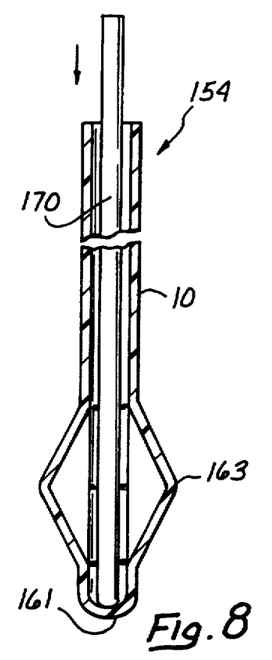
FIG. 8 is a side elevation view showing the distal end of the stylet engaging the distal end of the gastrostomy tube to facilitate stretching the tube along the length of the stylet.
Figure 10:
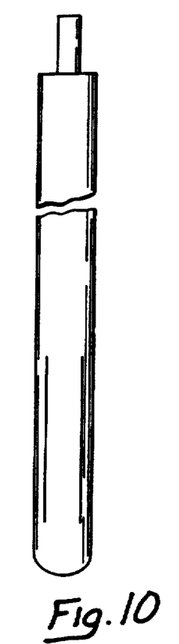
FIG. 10 is a side elevation view showing the feeding tube in a low profile state stretched along the length of the stylet and releasibly locked in the stretched state by the connector.
Figure 11:
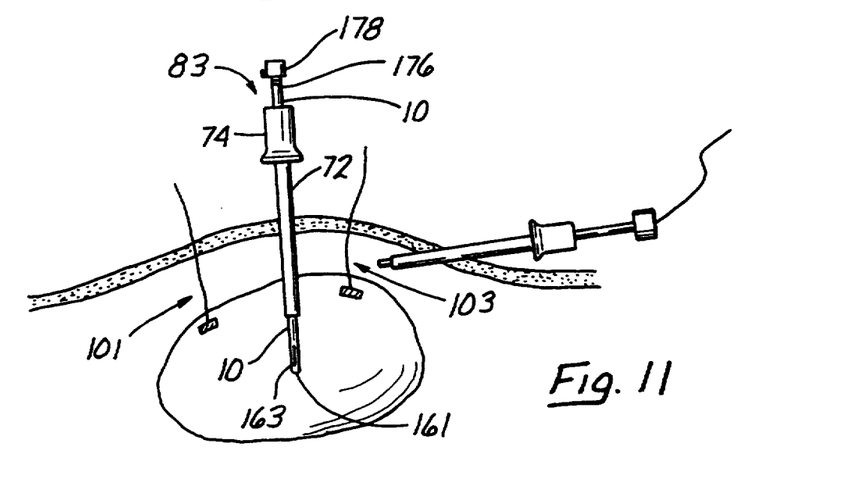
FIG. 11 is a side view similar to FIG. 3 illustrating the step for insertion of the stretched feeding tube through the cannula of the trocar.

The stylet 170 is of particular advantage in stretching or otherwise moving the feeding tube 10 between the normal high profile state illustrated in FIGS. 7a and 7b and the stretched low profile state illustrated in FIGS. 8 and 10. In the stretched state, the tube 10 will have a length greater than that in the normal state, and an outside diameter which is less than that in the normal state.

The stretching of the tube 10 can be accomplished in at least two ways using the stylet 170. In accordance with one method, the distal end of the stylet 170 is inserted through one of the slots 165 to engage the wall 161 at the distal end 156 of the tube 10. Drawing the proximal end 154 of the tube 10 along the stylet 170, will move the tube 10 from the normal high profile state to the stretched low profile state. In this stretched state, the tube 10 can be held in frictional relationship against the stylet 170 to maintain the stretched low profile configuration.

Figure 9:
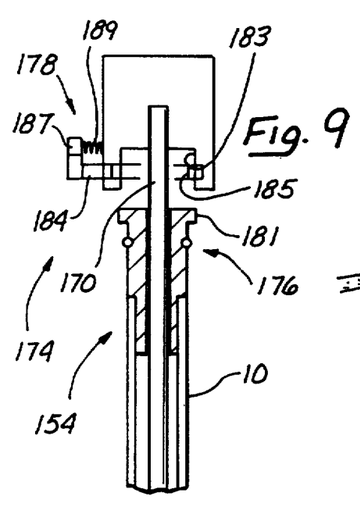
FIG. 9 is an axial cross-section view of a locking mechanism including a first portion attached to the proximal end of the feeding tube and a second portion releasibly lockable to the first portion of the connector and attached to the proximal end of the stylet.

The stretched state can be achieved and maintained with a different apparatus and method illustrated in FIGS. 9 and 10. This apparatus includes a locking mechanism or connector 174 having a first connector portion 176 and a second connector portion 178. As illustrated in FIG. 9, the first connector portion 176 can be fixed to the proximal end of the feeding tube 10 while the second connector portion 178 is fixed to the proximal end of the stylet 170. The connector 174 can be of a type manufactured by Colder Products of St. Paul, Minn., which is constructed so that the two connector portions 176 and 178 can be releasibly locked to each other.

This functional relationship is achieved in the preferred embodiment wherein the structure of the first connector portion 176 is generally cylindrical and includes a flange 181 which extends radially outwardly. For reasons discussed in greater detail below, the outside diameter of the flange 181 is preferably less than the inside diameter of the inner surface 81 of the cannula 72. The second connector portion 178 is provided with a recess 183 which has a diameter slightly larger than the flange 181. A locking flange 184 has a similar recess 185 and the same diameter as the recess 183. However, this locking flange 184 is movable radially between an unlocked position wherein the recesses 183 and 185 are axially aligned to receive the flange 181, and an unlocked position where the recesses 183 and 185 are misaligned to 3Lock the flange 181 in the recess 183. Radial movement of the locking flange 184 is facilitated by a tab 187 which is biased by a spring 189 to the locked position.

In operation, the stylet 170 can be inserted directly into the lumen 158 to engage the wall 161 at the distal end 156 of the tube 10. The first connector portion 176 can then be grasped and moved axially with the proximal end 154 of the tube 10, in the direction of the second connector portion 178. This stretches the tube 10 into the stretched low profile state illustrated in FIG. 10. In this state, the tab 187 and associated locking flange 184 of the second connector portion 178 can be moved against the bias of the spring 189 inwardly to receive the flange 181 of the first connector portion 176. Releasing the tab 187 moves the locking flange 184 to the locked position retaining the flange 181 in the recess 183. In this manner, the tube 10 can be releasibly locked in its stretched low profile state.

With the stylet 170 engaging the wall 161 as illustrated in FIGS. 8 and 10, the tube 10 in its low profile state can be inserted into the working channel 83 of the cannula 72.

Once the fingers 163 of the tube 10 have cleared the distal end of the cannula 72 within the stomach cavity 18, the tab 187 of the connector 174 can be operated to release the first connector portions 176 from the second connector portions 178. This will permit the elastomeric tube 10 to automatically retract from its stretched low profile state, and move along the stylet 170 to its normal high profile state. This movement will also permit the fingers 163 to expand radially outwardly to their normal state thereby forming an anchor for the tube 10 within the stomach cavity 18 as illustrated in FIG. 12.

Figure 12:
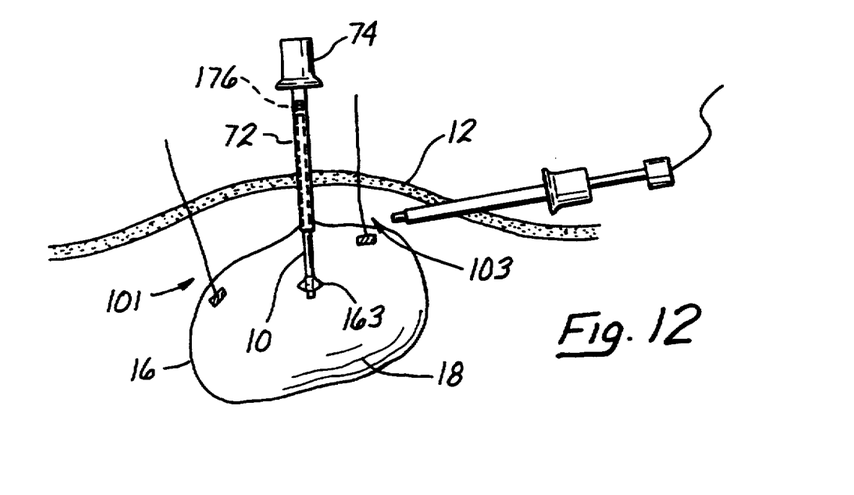
FIG. 12 is a side view similar to FIG. 3 showing the locking mechanism unlocked and the stylet removed from the feeding tube to achieve the high profile state, with the cannula of the trocar being removed over the distal end of the feeding tube.

If the first connector portion 176 is provided with a diameter not greater than the inside diameter of the inner surface 81, the cannula 72 can then be removed proximally over the tube 10 and the first connector portion 176 as illustrated in FIG. 12. Although there may be some frictional resistance to this relative movement, the fingers 163, functioning as an anchor, will tend to hold the tube in position across the abdominal wall 12 and the stomach wall 16.

If the tube 10 is provided with an outside diameter in its normal state which is greater than the outside diameter of the outer surface 87 of the cannula 72, then the tube 10 will automatically exert a pressure against the stomach wall 16 and the abdominal wall 12 as it attempts to become larger than the diameter of the holes left by the trocar 70. In effect, the tube 10 attempts to achieve an outside diameter which is greater than the inside diameter of the holes through which it extends. This provides excellent sealing characteristic which help to prevent leakage around the tube 10.

One of the final steps in the process relates to approximation between the stomach wall 16 and the abdominal wall 12. This approximation helps to develop an adhesion which will form scar tissue defining a single channel through the walls 12 and 16. Once this happens, the feeding tube 10 can be removed and replaced without further use of a trocar.

Figure 13:
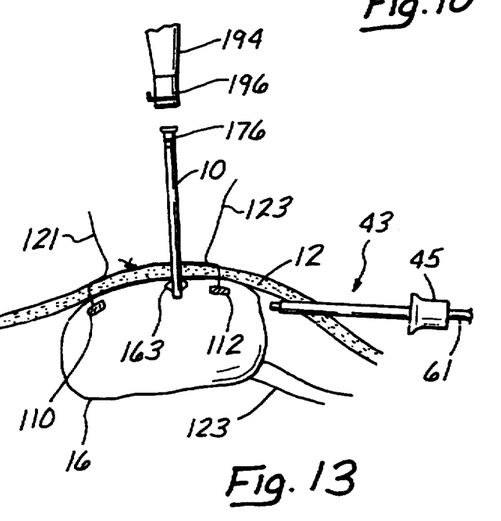
FIG. 13 is a side view similar to FIG. 1 and illustrating the approximation step wherein the stomach is brought into loose sealing engagement with the abdominal wall, and a funnel tip is applied to the proximal end of the feeding tube to facilitate the introduction of liquid nutrients and medicines into the stomach of the patient.

In this process of approximation, the sutures associated with the anchors 101-107 can be pulled to draw the associated T-bars and the stomach wall 16 against the abdominal wall 12. Thus, as illustrated in FIG. 13, the sutures 121 and 123 are pulled and tied together to maintain the walls 12 and 16 in juxtaposition. It is during this approximation step that the visualization provided by the endoscope 61 is of particular advantage. By viewing this procedure, the sutures 121 and 123 can be drawn sufficiently tight to bring the walls 12 and 16 into a snug sealing relationship without reducing circulation and promoting necrosis. Once the approximation step has been completed, the cannula 43 and the scope 61 can be removed from the abdominal wall 12.

If the first connector portion 176 is provided with a reduced diameter facilitating removal of the cannula 72, it may be desirable to provide an enlarged funnel 194 for attachment to the proximal end 154 of the tube 10. This funnel 194 will facilitate the administration of fluids to the patient 14. Attachment of the funnel 194 to the tube 10 is accomplished in the illustrated embodiment by providing an additional connector portion 196, similar to the connector portion 178, which will maintain the funnel 194 and the tube 10 in a releasibly locked relationship.

Although this invention has been described with reference to apparatus and methods associated with the gastrostomy tube 10, it will be apparent that these embodiments and processes can be varied to accommodate a different procedure providing percutaneous access to any internal body conduit. In general, an electrosurgical obturator will always be preferred for the trocars 41 and 70. These particular instruments provide for a reduced axial insertion force resulting in much greater control over the insertion process. Where the particular body conduit has a wall, such as the stomach wall 16, which is particularly difficult to penetrate, electrosurgical formation of the hole will be greatly appreciated.

The tube 10 can be formed from many different materials although an elastomeric material is preferred in order to take advantage of the stylet 170 and the resulting choice it offers between a high profile and a low profile state. Many types of connectors can also be used for maintaining the tube 10 in the stretched low profile state. Where the connector has two portions, such as the portions 176 and 178 illustrated in FIG. 9, the smaller of these two portions is preferred for attachment to the tube 10. This facilitates removal of the cannula 72 over the smaller connector portion 176 as illustrated in FIG. 12.

With the wide variations in the apparatus and methods which will now be apparent to persons of ordinary skill in this art, one is cautioned not to restrict the concept to the disclosed embodiments and method steps, but rather to determine the scope of the invention only with reference to the following claims.

We claim:
1. A combination, including:
a trocar for creating a hole into a body conduit;

a cannula included in the trocar and having a cylindrical wall with an outside diameter and an inside diameter;

an elastomeric tube having a channel extending between a proximal end and a distal end, the tube having in a normal state a first outside diameter greater than the outside diameter of the cannula and having in a stretched state a second outside diameter less than the inside diameter of the cannula;

a stylet sized and configured to engage the tube at the distal end of the tube, the stylet being operable to move the tube from the normal state to the stretched state so that the tube can be inserted into the cannula and through the cannula into the body conduit; whereby the stylet and the cannula can be removed from the tube leaving the tube extending through the hole into the body conduit with the tube in the normal state and its larger first outside diameter of the tube filling the hole left by the smaller outside diameter of the cannula.

2. The combination recited in claim 1 wherein:

the stylet has a proximal end and a distal end, and a length greater than the length of the tube in the normal state, the stylet having a diameter sufficiently small to fit through the channel of the tube to engage the distal end of the tube.

3. The combination recited in claim 2 further comprising:

a coupler including a first portion and a second portion the first portion of the coupler being releasibly lockable to the second portion of the coupler;

means for fixing the first portion of the coupler to the proximal end of the tube; and means for fixing the second portion of the coupler to the proximal end of the stylet; whereby the stylet can be inserted into the tube to engage the distal end of the tube, and the tube can be stretched to permit the first portion of the coupler to be releasibly locked to the second portion of the coupler with the tube in the stretched state.

4. A combination, including:

a tube having an elongate configuration and an axis extending between a proximal end and a distal end, the tube having walls defining a lumen along the axis and having elastomeric characteristics permitting the tube to be stretched axially between a normal high profile state wherein the walls of the tube have a first length and a first outside diameter and a stretched low profile state wherein the walls of the tube have a second length greater than the first length and a second outside diameter less than the first outside diameter;

a plug disposed along the axis of the tube at the distal end of the tube and having a generally fixed relationship with the walls of the tube;

an elongate stylet having a proximal end and a distal end separated by a length greater than the first length of the tube in the normal low profile state, the stylet being sized and configured to be inserted into the proximal end of the tube along the lumen of the tube to bring the distal end of the stylet into and engaging relationship with the plug at the distal end of the tube;

a connector including a first connector portion and a second connector portion adapted to be releasibly locked to the first connector portion;

the first connector portion being attached to the proximal end of the tube;

the second connector portion being attached to the proximal end of the stylet;

the tube having properties for being stretched along the stylet from its normal high profile state to its stretched low profile state; and means included in the connector for releasibly locking the first portion of the connector to the second portion of the connector to maintain the tube in its stretched low profile state.

5. The combination recited in claim 4 wherein the tube further comprises:

a plurality of fingers disposed around the circumference of the tube and extending longitudinally of the tube to support the plug at the distal end of the tube, the fingers extending generally outwardly of the tube in the natural high profile state and extending generally longitudinally of the tube in the stretched low profile state.

6. The combination recited in claim 4 wherein:

one of the first connector portions and the second connector portions comprises a cylinder fixed to the distal end of the tube and defining a lumen which is disposed coaxially of the lumen of the tube;

a flange extending radially of the cylinder;

the other of the first connector portion and the second connector portion comprising a second cylinder sized and configured to receive the first cylinder and to engage the flange of the first connector portion in a releasibly locked relationship.

7. The connector recited in claim 6 wherein:

the first connector portion is the one connector portion; and the second connector portion is the other of the connector portions.

8. A method for inserting a medical device through a hole into a body conduit, the hole having a particular diameter and the method comprising the steps of:

providing the medical device in the form of an elongate tube with an axis extending between a proximal end and a distal end, the tube having walls defining a lumen along the axis and elastomeric characteristics permitting the tube to be stretched axially between a natural high profile state wherein the walls of the tube have a first length and a first outside diameter and a stretched low profile state wherein the walls of the tube have a second length greater than the first length and a second outside diameter less than the first outside diameter;

providing a stylet having a proximal end and a distal end separated by a length greater than the first length of the tube in the natural high profile state;

engaging the distal end of the tube with the distal end of the stylet;

stretching the tube by moving the proximal end of the tube along the stylet;

locking the proximal end of the tube to the stylet with the tube in the stretched low profile state;

inserting the stylet and the tube in the stretched low profile state into the hole;

unlocking the proximal end of the tube from the stylet to permit the tube to return from the stretched low profile state to the natural high profile state;

disengaging the distal end of the stylet from the distal end of the tube; and removing the stylet from the hole leaving the tube extending through the hole into the body conduit with the tube in the natural high profile state.

9. A method for placing a catheter percutaneously into a body conduit disposed within the abdominal wall of a patient, comprising the steps of:

providing a trocar including a cannula and an obturator, the cannula having a cylindrical wall with an outside diameter and an inside diameter;

inserting the trocar through the abdominal wall and into the body conduit of the patient;

removing the obturator from the cannula of the trocar;

providing the catheter in the form of an elastomeric tube having a channel extending along the length of the tube between a proximal end and a distal end, the tube having in a normal state a first outside diameter greater than the outside diameter of the cannula and having in a stretched state a second outside diameter less than the inside diameter of the cannula;

providing a stylet having a length extending between a proximal end and a distal end, the length of the stylet being greater than the first length of the tube in the normal state;

stretching the tube along the stylet from the normal state to the stretched state;

inserting the stretched tube in the stretched state through the cannula of the trocar and into the body conduit;

removing the stylet from the tube leaving the tube in the cannula of the trocar; and removing the cannula from the tube leaving the tube extending percutaneously through the abdominal wall and into the body conduit of the patient.

10. The method recited in claim 9 wherein the inserting step comprises the steps of:

moving the trocar through the abdominal wall;
removing the obturator from the cannula;
inserting graspers into the cannula;
grasping the body conduit within the abdominal wall;
moving the body conduit toward the abdominal wall;
holding the body conduit in proximity to the abdominal wall;
removing the graspers from the cannula;
reinserting the obturator into the cannula; and
moving the trocar into the body conduit within the abdominal wall.

11. The method recited in claim 9 wherein the body conduit is the stomach of the patient and the tube is a gastrostomy tube.

12. The method recited in claim 9 further comprising the steps of:

during the step of providing a trocar, providing the obturator with an electrical conductor responsive to an electrosurgical current;

during the first moving step, electrosurgically energizing the conductor on the trocar to create a first hole in the abdominal wall and moving the cannula of the trocar through the first hole in the abdominal wall; and during the second moving step, electrosurgically energizing the conductor of the obturator to create a second hole in the body conduit and moving the cannula of the trocar through the second hole into the body conduit.

13. The method recited in claim 8 further comprising the steps of:

providing the tube with an annular flange at the proximal end of the tube;

providing the stylet with a locking flange at the proximal end of the stylet, the locking flange being movable between a locked position and a released position; and the locking step includes the step of engaging the annular flange at the proximal end of the tube with the locking flange at the proximal end of the stylet to lock the tube to the tube in the stretched, low-profile state.

14. The method recited in claim 13 wherein:

the method further comprises the steps of biasing the locking flange to the locked position; and the unlocking step includes the step of moving the locking flange against the bias from the locked position to the released position to permit the tube to return from the stretched low-profile state to the natural high-profile state.

15. A method for accessing an interior region of an organ disposed within a body wall, the organ having in a natural state, a generally loose, distant relationship with the body wall, comprising the steps of:

providing a trocar having a cannula and an obturator;

inserting the trocar through the body wall with the obturator positioned within the cannula of the trocar;

grasping the organ;

maintaining at least a portion of the organ in an operative state wherein the organ has a more fixed and a more proximate relationship with the body wall than in the natural state;

inserting the trocar into the organ to access the interior region of the organ with the obturator disposed in the cannula of the trocar; and removing the obturator from the cannula leaving the cannula in place to define a passage across the body wall and into the interior region of the organ.

16. The method recited in claim 15 wherein the maintaining step includes the step of anchoring at least the portion of the organ to the body wall.

17. The method recited in claim 16 wherein the anchoring step includes the step of:

inserting a plurality of anchors through the body wall and into the organ; and moving the anchors to draw the organ from the natural state to the operative state.

18. The method recited in claim 17 wherein:

the step of inserting a plurality of anchors includes the step of inserting the anchors into the organ in a pattern wherein the anchors define a particular area of the organ; and the step of inserting the trocar into the organ includes the step of inserting the trocar through the particular area of the organ.

19. The method recited in claim 18 wherein the particular area has a plurality of corners and the step of inserting a plurality of anchors includes inserting one of the anchors into the organ at each of the corners of the particular area.

20. The method recited in claim 15 wherein the step for inserting the trocar into the organ includes the steps of:

electrosurgically activating the obturator; and while the obturator is electrosurgically activated, moving the trocar into the interior region of the organ.

* * * * *

UNITED STATES PATENT AND TRADEMARK OFFICE
CERTIFICATE OF CORRECTION

PATENT NO. : 5,429,598

DATED : July 4, 1995

INVENTOR(S) : Waxman etal

It is certified that error appears in the above-identified patent and that said Letters Patent is hereby corrected as shown below:

Col. 1, line 55, change the word "sever" to -- severe, --;

Col. 6, line 33, after the word "wall" delete the numeral "18" and add the numeral -- 16 --;

Col. 6, line 59, after the word "monitor" delete the numeral "65" and add the numeral -- 60 --;

Col. 7, line 10, after the word "and" add the word "a";

Col. 7, line 24, after the word "wall" delete the numeral "18" and add the numeral -- 16 --.

Col. 8, line 15, after the word "Figure" delete the numeral "7b" and add the numeral -- 7a --;

Col. 8, line 39, after the numeral "7a" delete the phrase "and 7b"; and

Col. 11, line 60, before the word "low" delete the word "normal" and add the word -- stretched --.

Signed and Sealed this

Ninth Day of January, 1996

*Attest:*

BRUCE LEHMAN

*Attesting Officer*     Commissioner of Patents and Trademarks